United States Patent [19]

Piontek et al.

[11] Patent Number: 5,098,378
[45] Date of Patent: Mar. 24, 1992

[54] METHOD OF JEJUNAL FEEDING

[75] Inventors: Carl J. Piontek, Powell; Kent E. Iversen; William H. Hirsch, both of Columbus; Arthur A. Dahl, Westerville, all of Ohio

[73] Assignee: Abbott Laboratories, Abbott Park, Ill.

[21] Appl. No.: 732,965

[22] Filed: Jul. 19, 1991

Related U.S. Application Data

[62] Division of Ser. No. 360,814, Jun. 2, 1989.

[51] Int. Cl.$^5$ .............................................. A61M 31/00
[52] U.S. Cl. ....................................................... 604/49
[58] Field of Search ................... 604/49, 96, 158, 174, 604/178, 264

[56] References Cited

U.S. PATENT DOCUMENTS

| | | | |
|---|---|---|---|
| 2,457,244 | 12/1948 | Lamson | 604/96 |
| 2,936,761 | 5/1960 | Snyder | 604/96 |
| 3,915,171 | 10/1975 | Shermeta | 604/101 |
| 4,004,588 | 1/1977 | Alexander | 604/96 |
| 4,057,065 | 11/1977 | Thow | 604/101 |
| 4,393,873 | 7/1983 | Nawash et al. | 604/151 |
| 4,516,968 | 5/1985 | Marshall et al. | 604/174 |
| 4,543,089 | 9/1985 | Moss | 604/96 |
| 4,624,657 | 11/1986 | Gould et al. | 604/96 |
| 4,685,901 | 8/1987 | Parks | 604/96 |
| 4,701,163 | 10/1987 | Parks | 604/178 |

FOREIGN PATENT DOCUMENTS 364721 of 1981 Austria.
1547328 of 1979 United Kingdom .................. 604/96

OTHER PUBLICATIONS

Moss, "Efficient Gastroduodenal (Decompression with Simultaneous Full Enteral Nutrition: A New Gastrostomy Catheter Technique", *Journal of Parenteral and Enternal Nutrition*, vol. 8, No. 2: 203-207.

*Primary Examiner*—John D. Yasko
*Assistant Examiner*—Anthony Gutowski
*Attorney, Agent, or Firm*—Lonnie R. Drayer; Donald O. Nickey

[57] ABSTRACT

A replacement gastrostomy tube device is provided comprising a catheter shaft having an outer surface wall, with the shaft enclosing a feeding lumen of substantially circular cross-section and a fluid flow channel. A port housing is located at the proximal end of the shaft with the port housing having a main food inlet port, a Y-port and a fluid inlet port. Near the distal end of the tube are an expandable component member and a food outlet port, which port is preferably located at the distal end. The feeding lumen is of a greater diameter than that of the fluid flow channel. The outer surface wall is of a non-circular cross-section. The feeding lumen is of a circular cross-section which permits the passage therethrough of a jejunal tube. The main food inlet port is of a greater diameter than that associated with the Y-port. The method for using this device permits jejunal feeding through a replacement gastrostomy tube without retraumatizing the patient.

1 Claim, 5 Drawing Sheets

METHOD OF JEJUNAL FEEDING

This is a divisional of application Ser. No. 07/360,814 filed on June 2, 1989 (pending).

TECHNICAL FIELD

The present invention relates generally to a feeding tube, and more particularly, to an improved replacement gastrostomy tube which can accommodate internal passage of a secondary jejunal feeding tube.

BACKGROUND OF THE INVENTION

Most patients in health care facilities are able to achieve sufficient caloric intake through eating prepared meals. However, a sizable number of such patients are unable to ingest enough food to meet their body's needs. Examples of these individuals would include burn patients, whose daily caloric needs are often in excess of 5,000 calories; critically ill, weak or comatose patients, who may be unable to chew their food., and patients suffering from cancer of the esophagus, who may be unable to swallow their food. For these patients, parenteral caloric supplementation, also known as intravenous feeding, is not a viable alternative.

In response to this problem, liquid foods have been developed for enteral feeding. Enteral feeding often utilizes a nasogastric tube to transport the liquid nutritional products from a container through the patient's nasal cavity and thence into the stomach. However, an increasing number of ambulatory patients utilize and prefer direct enteral feeding through gastrostomy devices.

While it is possible to place a primary gastrostomy device by means of a surgical procedure utilizing a general anesthetic, the preferred method for placement of these devices is through a percutaneous endoscopic gastrostomy (PEG) which involves the non-invasive, non-surgical creation of an artificial opening or stoma into the stomach through the abdominal wall using only local anesthetic. In a representative PEG procedure, an endoscope is passed down the throat until its terminus contacts the interior of the stomach wall. A needle, with stylet in place, is then inserted through the various tissue layers until it enters the stomach at a predetermined point. The stylet of the needle is retracted and a guidewire is then inserted through the cannula of the needle.

The terminal end of the guidewire (now inside the stomach) is grasped using an endoscopic appliance and retracted up the throat. A primary gastrostomy tube is then inserted with the assistance of the guidewire so as to provide a direct enteral feeding conduit to the patient's gastric system.

To better understand the advantages associated with the instant invention, it is necessary to appreciate the distinctions between primary and secondary gastrostomy tubes. A primary gastrostomy tube, is the device used for the initial placement in the patient of a gastric enteral feeding tube. With a length of approximately 1 meter the primary tube has as its principle focus, the forming of a healthy stoma tract. In contrast, the approximately 225 mm secondary gastrostomy tube, assumes the presence of a healthy stoma tract and, in fact, is able to be physically pushed into position through an open stoma, following removal of the primary gastrostomy tube. Reasons why the primary gastrostomy tube may have to be removed include clogging due to the viscous character of enteral nutritional food product, the perforation of the mucosa wall, or just deterioration due to age. Primary gastrostomy tubes usually only last on average from three to twelve months. Additionally, the patient may accidentally or intentionally pull the primary tube out, thus requiring the insertion of a replacement tube. The prior art replacement gastrostomy devices comprise a catheter shaft enclosing a non-circular feeding lumen and a fluid flow channel with the fluid flow channel permitting the filling of an expandable component member so as to provide for the securing of the device with respect to the stomach wall.

In both primary and secondary gastrostomy tubes, a main feeding port permits the introduction of enteral nutritional product into the feeding lumen and thence into the stomach. The main feeding port is connected to a supply of nutritional product via an adapter set which accommodates various sizes of tubing. The devices according to the prior art provide only one access to the feeding lumen. As a result, these devices cannot be used for other than feeding purposes without disconnecting the pump set.

One aspect of the present invention resides in the "Y-port" connector which provides access to the feeding lumen for non-feeding purposes. Possible reasons for non-feeding access include gastric suction, decompression, the introduction of medication in the form of crushed pills or liquid, and maintenance associated with the gastrostomy tube. In gastric suction, the gastric contents of the stomach or small bowel are retrieved. Examples of such gastric contents could include mucous, air, bile, gastric juices or feeding residue. The retrieval of gastric residual content is extremely important for numerous reasons, including the determination of the proper rate of feeding. Health care professionals would find this feature extremely beneficial, since the prior art devices do not possess such a feature.

Individuals who utilize primary or secondary gastrostomy devices may encounter problems with a condition known as reflux. In reflux, the gastric residual is refluxed or vomited up the esophagus. In a weak or bedridden patient, or one who has no ability to swallow normally, reflux may result in the gastric residual being inhaled into the lungs and death from aspiration pneumonia can result. In order to provide gastric suction or introduce medication into the feeding lumen using prior art devices, it is necessary to disconnect the pump set or provide multiple hookups and thereby risk the problem of contamination.

For individuals who frequently encounter or are prone to problems with reflux, feeding can be accomplished by the use of a jejunal feeding tube which passes through the stomach, the pylorus and then enters the small bowel, the duodenum and the jejunum. However, a problem is encountered by patients attempting to use jejunal tubes with prior art replacement gastrostomy tubes in that the prior art failed to appreciate the problem of retraumatization.

Retraumatization, in addition to causing discomfort, also has the danger of infection and the potential for bleeding occurring due to the sensitive tissue present at the stoma. As a result of not appreciating the problem of retraumatization, replacement gastrostomy tubes have been designed with a circular outer cross-section and a non-circular cross-section for the feeding lumen and therefore jejunal tubes can not be inserted therethrough.

Consequently, in cases where it becomes necessary for a patient with a secondary gastrostomy tube to be fed by the use of a jejunal feeding tube, the health care professional is typically confronted by three options, all of which will subject the patient to significant retraumatization. The first option is to remove the secondary gastrostomy tube and to replace it with another primary gastrostomy tube using a PEG procedure. The second option is to forcibly insert a larger outer diameter secondary gastrostomy tube through the stoma, in the hope that a sufficiently large inner diameter will be provided to permit the passage therethrough of a jejunal tube. The third option is to surgically perform a jejunostomy, and insert the jejunal tube while the patient is under a general anesthetic. The only option available which will temporarily avoid retraumatization is to try to use a jejunal tube of a small French size with the existing replacement gastrostomy tube, however, this often results in clogging, especially in milk-based nutritional feeding products, so as to restrict or preclude feeding, thus ultimately necessitating removal of the replacement gastrostomy tube and the retraumatizing of the patient by one of the three aforementioned options.

Yet another problem encountered in gastrostomy tubes is that of kink resistance. When a tube kinks, its internal walls tend to collapse and fold upon the opposite side of the tube. This condition normally happens accidentally, as the patient turns in bed, but the result is that fluid flow is restricted or curtailed altogether. To increase kink resistance associated with a specific tube, the distance between the inner diameter of the catheter shaft and the outer diameter of the catheter shaft can be increased. However, too much of an increase in the thickness of the tube wall renders the tube inflexible, and reduces the feeding area associated with the feeding lumen for a device of a given outside diameter.

Examples of prior art gastrostomy feeding devices are shown in Parks U.S. Pat. Nos. 4,701,163 and 4,685,901. U.S. '163 device fails to appreciate the need for additional access to the feeding lumen. The configuration of the '163 feeding lumen (i.e. cross section) will not allow the passage of a J-tube.

U.S. Pat. No. 2,457,244 relates to a medical appliance for control of enemata. The medical appliance of U.S.'244 comprises an inflatable element upon the forward end of a pipe and a means operating to fit snuggly against the anus of the patient and in consequence hold the inflated balloon against the internal mouth of the anal canal. Of particular interest is FIG. 3 of the '244 patent which illustrates a common non-circular cross section of tubes utilizing an inflatable member.

Austrian patent No. 364,721 relates to a catheter for establishing a fluid line between the exterior of the body and the bladder or the renal pelvis in the form of a hose which is surrounded by a dilatable means which can be expanded after introduction into the interior of the body, said hose having an extension which protrudes from the dilatable means. This patent fails to consider the specific needs for replacement or secondary feeding tubes. Specifically, this reference fails to suggest a Y-port for the feeding lumen and the need for J-tube insertion after the tube is in place.

U.S. Pat. No. 3,915,171 relates to a gastrostomy tube for insertion into the stomach and for retention as a consequence of bearing engagement against the inside stomach wall and the outside abdominal wall. The patent also discloses a conduit which carries a stiffly flexible retention bulb which can be collapsed by a stylet for insertion through a stab wound through the stomach. In the stomach the bulb resumes its normal shape when the stylet is withdrawn. The device disclosed in this reference would not permit the passage of a J-tube.

U.S. Pat. No. 4,516,968 discloses a catheter shield and method of use. U.S. Pat. No. 4,393,873 relates to gastrostomy and other percutaneous transport tubes which contain anti-reflex valves. Both of these references fail to disclose the device of the instant invention which allows for the passage of a J-tube and access to the feeding lumen without disconnecting the feed set.

An article by Gerald Moss in the Journal of Parenteral and Enteral Nutrition, Vol. 8, No. 2 entitled "Efficient Gastroduodenal Decompression with Simultaneous Full Enteral Nutrition: A New Gastrostomy Catheter Techniques" discloses a gastrostomy tube designed to provide efficient supplemental aspiration of the proximal duodenum to remove gas that escapes gastric removal, utilizing an extension of the gastric suction channel.

It is thus apparent that the need exists for an improved replacement gastrostomy tube. The prior art fails to suggest or disclose an improved replacement tube which provides additional means of access to the feeding lumen, permits the use of jejunal tubes, and maximizes the feeding area of the tube, while at the same time overcoming additional drawbacks associated with existing replacement gastrostomy tubes.

DISCLOSURE OF THE INVENTION

There is disclosed a replacement gastrostomy tube device comprising, a catheter shaft, said shaft having an outer surface wall, said shaft enclosing a feeding lumen of substantially circular cross-section which permits the passage there through of a jejunal tube and a fluid flow channel, said shaft having a proximal end and a distal end, a port housing located at said proximal end, said port housing having a main food inlet port, a Y-port, and a fluid inlet port, an expandable component member, and a food outlet port located at said distal end.

Additionally, the feeding lumen is of a first diameter and the fluid flow channel is of a second diameter, with the first diameter being greater than the second diameter. Also, preferably the food outlet port is the sole food outlet port in the shaft. Further, the outer surface wall of the shaft is of a non-circular cross-section.

There is also disclosed a replacement gastrostomy tube device comprising a catheter shaft, said shaft having an outer surface wall of non-circular cross-section, said shaft enclosing a feeding lumen of substantially circular cross-section and a fluid flow channel having an end wall, wherein said feeding lumen is of a first diameter and said fluid flow channel is of a second diameter, said first diameter being greater than said second diameter, said feeding lumen permitting the passage therethrough of a jejunal tube, said shaft having a proximal end and a distal end, a port housing located at said proximal end, said port housing having a main food inlet port, a Y-port, and a fluid inlet port, an expandable component member located between said food outlet port and said port housing, a retention device located between said expandable component member and said port housing, and a food outlet port located at said distal end, said food outlet port being the sole food outlet port in said shaft.

There is further disclosed a method for jejunal feeding, comprising, inserting a replacement gastrostomy tube through a stoma and into a patient's stomach, and inserting a jejunal tube through said replacement gastrostomy tube and into the jejunum, said replacement gastrostomy tube device comprising, a catheter shaft, said shaft having an outer surface wall, said shaft enclosing a feeding lumen of substantially circular cross-section and a fluid flow channel, said shaft having a proximal end and a distal end, a port housing located at said proximal end, said port housing having a main food inlet port, a Y-port, and a fluid inlet port, an expandable component member, a retention device located between said expandable component member and said port housing, and a food outlet port located at said distal end, whereby said expandable component member, when expanded, cooperates with said retention device to prevent the undesirable movement of the replacement gastrostomy tube further into the stomach or the undesirable withdrawal of said replacement gastrostomy tube through said stoma.

The present invention provides a replacement gastrostomy tube which provides direct supplemental access to the feeding lumen without disconnecting of the pump set, as well as permitting the insertion of a jejunal tube without retraumatizing the patient. The device of the present invention overcomes the drawbacks associated with existing replacement gastrostomy tube devices and advances the state of the art of enteral feeding devices and methodologies.

Other aspects and advantages of the invention will be apparent from the following description, the accompanying drawings and the appended claims.

DETAILED DESCRIPTION OF THE INVENTION

Figure 1:
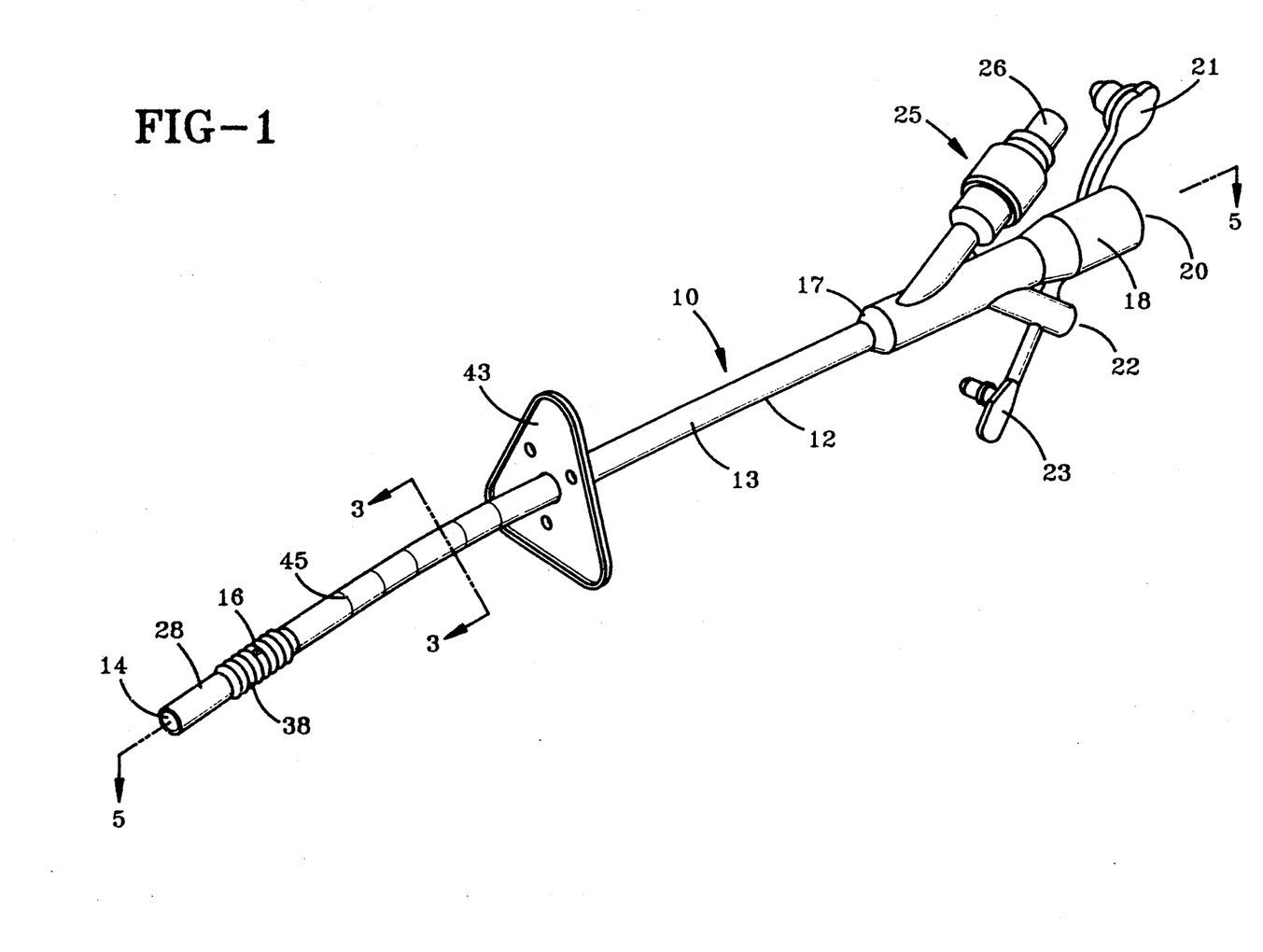
FIG. 1 is a perspective view of the gastrostomy tube device in accordance with the present invention.

Having reference to the drawings, attention is directed first to FIG. 1 which illustrates a gastrostomy tube device embodying this invention designated generally by the numeral 10. The basic components of this device are a catheter shaft 12 having an outer surface wall 13, with the shaft 12 enclosing a feeding lumen 14 and a fluid flow channel 16. The fluid flow channel 16 is also referred to in the trade as a balloon lumen.

At the proximal end 17 of the catheter shaft 12 is port housing 18. The port housing includes as its primary components, a main food inlet port 20 equipped with a main port closure 21, a Y-port 22 similarly equipped with a Y-port closure 23, and a fluid inlet port 25 equipped with a valve means 26 preferably of the type known as a one-way valve.

Figure 2:
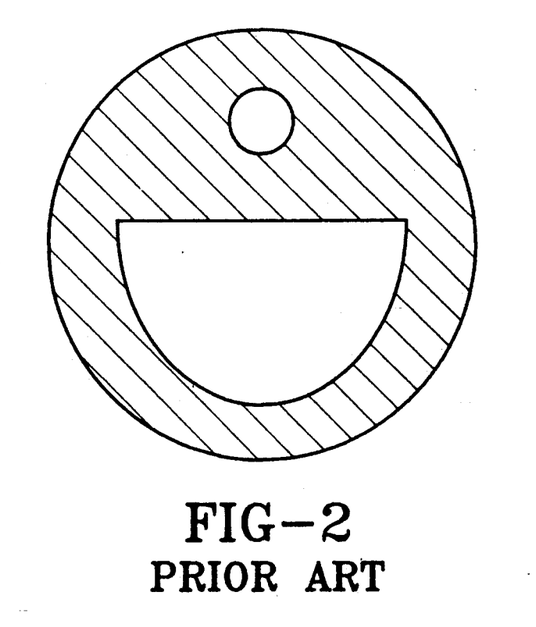
FIG. 2 is a vertical view of the catheter of a prior art replacement gastrostomy tube device.

In contrast to the instant invention, FIG. 2 discloses the cross-section of a prior art replacement tube similar to those described in U.S Pat. Nos. 4,701,163 and 4,635,901. The outer surface of the catheter and the enclosed fluid flow channel are circular, while the area associated with the feeding lumen is truncated. The wall between the feeding lumen and the outer surface wall thus has a tendency to be relatively thick in the area surrounding the fluid flow channel. With such a non-circular feeding lumen surface, the application of stress tends to facilitate kinking.

Figure 3:
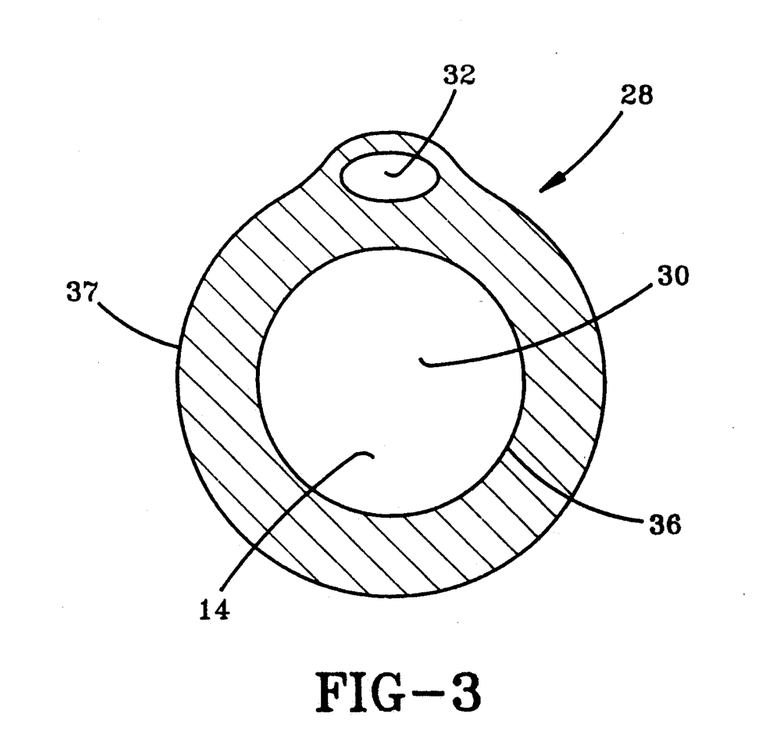
FIG. 3 is a vertical cross sectional view taken along 3—3 of FIG. 1.
Figure 4:
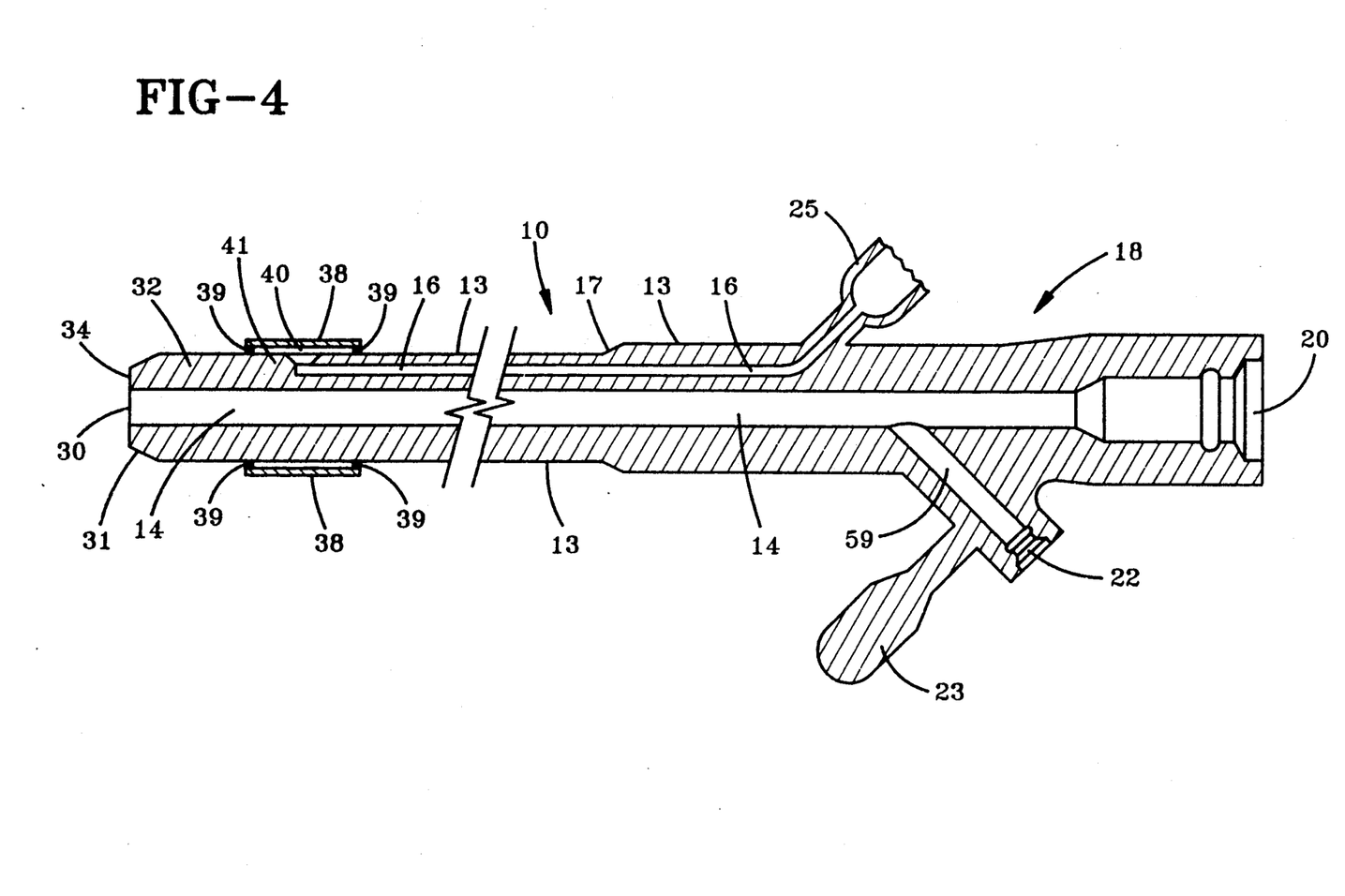
FIG. 4 is a vertical sectional view taken on a greatly enlarged scale along line 5—5 of FIG. 1.

As can be better seen in FIGS. 3 and 4, at the distal end 28 of the flexible catheter shaft 12 is food outlet port 30. The distal end 28 of shaft 12 has a beveled or tapered end portion 31 in which is recessed a non-functioning aperture 32. The beveled or tapered end portion 31 extends between flat end portion 34 and outer surface wall 13. As can best be appreciated by FIGS. 3 and 4, the outlet port 30 is of a circular cross-section 36, while the catheter shaft 12 is of a non-circular cross-section 37.

FIG. 4 discloses that an expandable component member 38, often referred to as a balloon, is secured preferably by means of an adhesive bond 39 to outer surface wall 13. A fluid access port 40 extends between the fluid flow channel 16 and the outer surface wall 13 located centrally of the expandable component member. An end wall 41 provides sealing off of that portion of the channel 16 from the non-functioning portion which now merely discloses the presence of aperture 32. As such, the fluid flow channel is capable of passing fluid from the valve means 26 {shown in FIG. 1} into expandable component member 38 so as to permit the expansion of the balloon.

Figure 5:
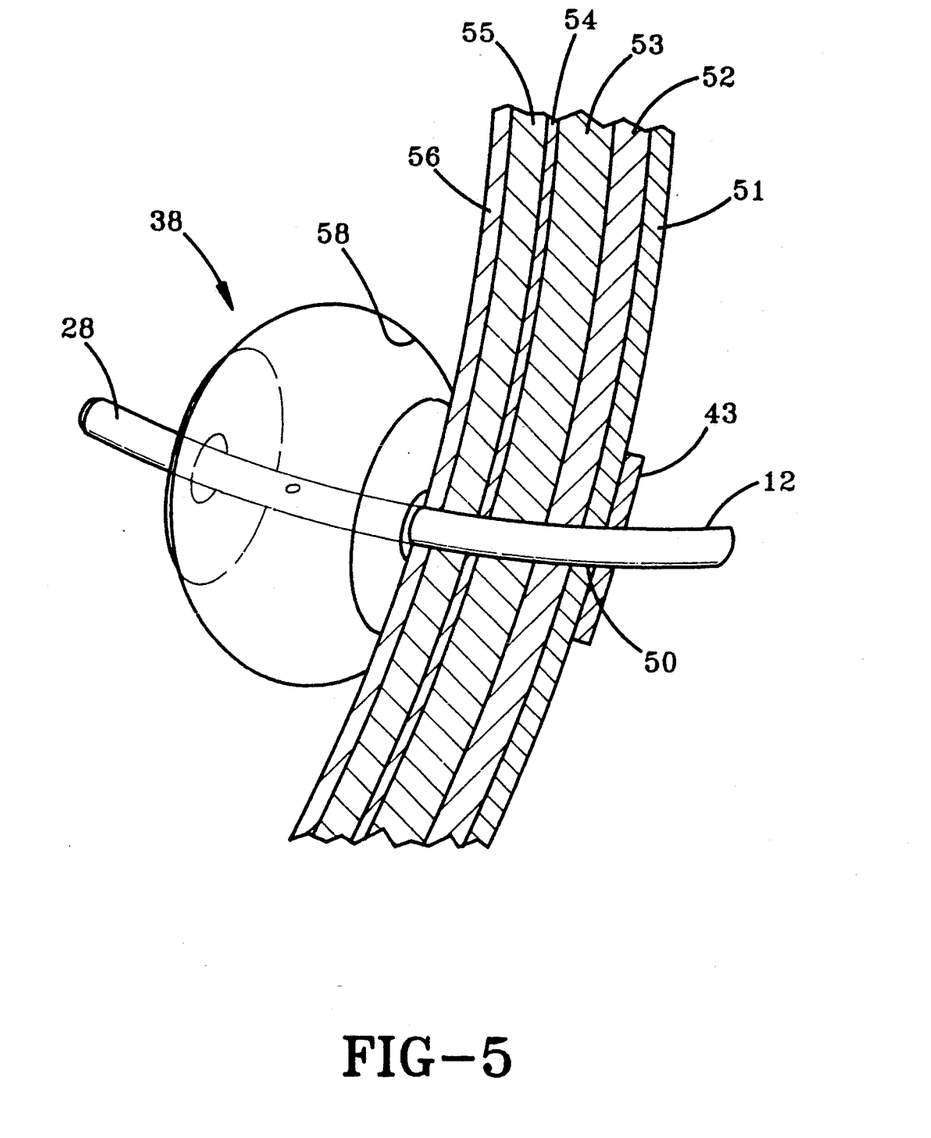
FIG. 5 is a perspective view, partly broken away, of the device installed in a patient.

As can be seen in FIGS. 1 and 5, a retention device 43 is also provided having a triangular configuration and a plurality of vent holes. The configuration of the retention device is not critical and those skilled in the art will appreciate that various designs are operable in the instant invention. Additionally, the outer surface wall 13 has a plurality of indicia 45 to assist with operation of the retention device 43. The indicia 45 serves the important function of allowing health care personnel to monitor tube placement. It has been found that proper tension must be placed on the feeding tube between the inflated member 38 and the retention device 43 so as to fix the feeding tube in the stoma. Insufficient tension in combination with the weight of the fluid-filled balloon 38 and normal peristalsis of the stomach will result in movement of the feeding tube into the body. It is possible that the feeding tube could eventually pass the pyloric sphincter and enter the small bowel. Feeding rates appropriate for the stomach are not normally tolerated in the small bowel. The patient is thereby subjected to intestinal overload which causes diarrhea, dehydration, and eventually leads to mineral and nutrient loss. Excessive tension will result in pressure necrosis and ulceration of the stomach mucosa can result over time. Also, as the patient goes from a malnourished to a nourished state, there is often a substantial weight gain. If tension is not reduced, then pressure necrosis can result. The indicia 45 permits the health care provider to monitor tube placement and thus prevent migration of the feeding tube into or out of the stoma tract.

The invention is preferably fabricated from 100% medical grade silicone, with the exception of the components of the valve means 26.

BEST MODE

In actual operation, the gastrostomy tube 10 of this invention is inserted through an artificial opening or stoma 50, created by a percutaneous endoscopic gastrostomy. The tube of this invention is intended to serve as a replacement gastrostomy tube. The distal end 28 of the catheter shaft 12 as well as the then unexpanded expandable component member 38 pass through a plurality of tissue layers: the epidermis 51, fat 52, muscle layer 53, peritoneum 54, and ultimately through stomach lining 55 and mucosa wall 56 as set forth in FIG. 5.

Once the balloon portion of the tube has entered the stomach, the balloon 38 is expanded using conventional means in cooperation with valve means 26. Such conventional expansion means often make use of a syringe, especially one filled with saline solution. The catheter shaft is then retracted through the stoma 50 as far as possible until the proximal wall portion 58 of the expandable component member 38 comes into contact with mucosa wall 56. The balloon "sits" into or comes in contact with the mucosa wall thereby forming a sealing mechanism for the stoma 50. The retention device 43 may then be placed directly adjacent epidermis 51 as is shown in FIG. 5. Cooperation between the expandable component member and the retention device places the proper tension on the tube which prevents the undesirable movement of the gastrostomy tube further into the stomach or the undesirable withdrawal of the gastrostomy tube through the stoma.

Feeding may then commence by the securing of an enteral feeding set adapter (not shown) to the main port 20. In the event that medication needs to be administered or that gastric suction must occur, access is provided to the feeding lumen through Y-port 22 and a Y-port channel 59 as shown in FIG. 4. Additionally, as can be seen, the diameter of the main port is greater than that of the Y-port 22 such that the gastrostomy tube of this invention permits immediate adaptation to smaller feeding adapters without the necessity of disconnecting the pump set from the main port, adding an adapter and thereby risking potential contamination.

Figure 6:
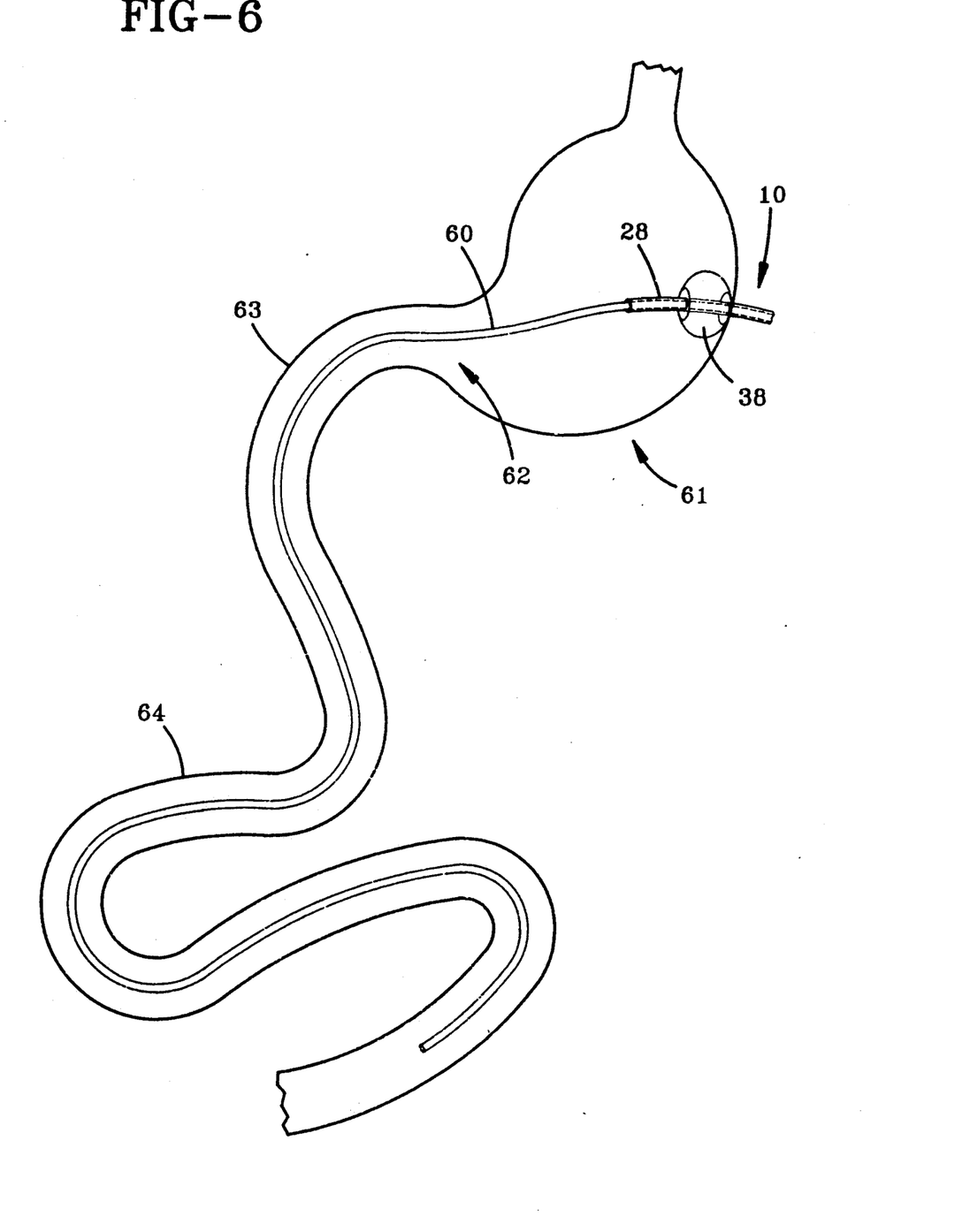
FIG. 6 is a perspective view of the gastrostomy tube used in conjunction with a jejunal tube to permit jejunal feeding.

Another important aspect associated with this invention is its ability, due to the substantially circular cross-section 36 of feeding lumen 14, to easily accommodate a jejunal tube 60 as is shown in FIG. 6. Nine and twelve French "J" or jejunal tubes can be accommodated in a "G" or gastrostomy tube with respective sizes of 14 and 18 French if constructed in accordance with this invention. The jejunal tube passes through the gastrostomy tube of this invention thence through the stomach, past the pylorus, and into the small bowel. Once in the small bowel, the jejunal tube 60 passes through the duodenum 63 and preferably terminates in the area of the jejunum 64.

Yet another important advantage associated with this invention is the reduced kinking radius associated with the catheter. One aspect of this invention resides in the discovery that by providing a feeding lumen of circular cross-section, the catheter is able to have increased kink resistance for a given outer diameter. The inventors herein have determined that increased kink resistance is achieved when the inside diameter of the feeding lumen is 64 to 72% of the outer diameter of the catheter. When a gastrostomy tube is replaced, proper sizing of the replacement tube is critical. The stoma is measured (usually using French sizes) and the largest outside diameter tube that will fit inside the stoma is chosen. For a given outside diameter it is desirable to have as large an inside diameter or feeding lumen as possible. A large inside diameter tube will lessen the changes of occlusion which is the primary cause of tube replacement.

It is also desirable that the tube not kink when subjected to ordinary movements of the patient. A kink in the feeding tube occludes the feeding lumen and thus prevents proper patient feeding. Kink resistance is typically measured in terms of kink radius. Kink radius is determined by bending the feeding tube around mandrels of decreasing diameter until it kinks. In general, the thicker the tube wall, the lower the kink radius. However, increasing wall thickness decreases the feeding lumen size for a given outside diameter.

The inventors herein, through experimentation and observation, have determined that for a given outside diameter the inside diameter of the feeding lumen should be from 64 to 72% of the outside diameter. This 64 to 72% of the outside diameter for the inside diameter of the feeding lumen provides maximum feeding lumen inside diameter without sacrificing kink resistance and forms one aspect of the present invention.

INDUSTRIAL APPLICABILITY

Over 20,000 Americans are currently being fed via gastrostomy tubes. The enteral feeding industry has long sought ways to reduce retraumatization, especially when a patient must be fed by a jejunal tube instead of solely by a gastrostomy tube. Until now, the decision to utilize a jejunal tube has been coupled with the necessity of retraumatizing the patient to replace the gastrostomy tube then in use. Additionally, the industry has sought ways to minimize the potential for contamination due to multiple hookups to a pump set and to permit gastric suction without disconnecting the patient from the pump set. This invention solves these long felt needs. All the advantages of this invention would be found extremely beneficial by physicians and health care providers.

While the form of apparatus and method herein described constitute a preferred embodiment of this invention, it is to be understood that the invention is not limited to this precise form of apparatus or method and that changes may be made therein without departing from the scope of the invention which is defined in the appended claims.

What is claimed is:

1. A method for jejunal feeding, comprising the steps of: (a) inserting a replacement gastrostomy tube through a stoma and into a patient's stomach, said replacement gastrostomy tube comprising (i) a catheter shaft, said shaft having a wall with an outer surface, a proximal end and a distal end, said shaft enclosing a feeding lumen having a circular cross-section, and a fluid flow channel embedded within the wall of the shaft, the inside diameter of the feeding lumen being 64% to 72% of the outside diameter of the catheter shaft, a food outlet port of said lumen located at the distal end of said catheter shaft, (ii) a port housing located at said proximal end of the catheter shaft, said port housing having a main food inlet port which communicates with said feeding lumen, a Y-port providing access to said feeding lumen through a Y-port channel, and a fluid inlet port which communicates with said fluid flow channel, (iii) an expandable a component member which is expandable when a fluid is injected therein is secured to the outer surface of said shaft wall with said fluid flow channel opening into the expandable component member, said expandable component member being located between said food outlet port and said port and said port housing, (iv) a retention device located between said expandable component member and said port housing; (b) injecting a fluid into said expandable component member, such that said expandable component member cooperates with said retention device to prevent the undesirable movement of said gastrostomy tube further into the stomach or the unintentional withdrawal of said gastrostomy tube through said stoma; and (c) passing a jejunal tube through the feeding lumen of said replacement gastrostomy tube and into the jejunum.

* * * * *